United States Patent [19]

Clauss

[11] Patent Number: 4,717,463
[45] Date of Patent: Jan. 5, 1988

[54] OXYGEN SENSOR

[75] Inventor: Harry G. Clauss, Wexford, Pa.

[73] Assignee: General Signal Corporation, Stamford, Conn.

[21] Appl. No.: 6,302

[22] Filed: Jan. 15, 1987

Related U.S. Application Data

[63] Continuation of Ser. No. 862,735, May 13, 1986, abandoned.

[51] Int. Cl.$^4$ .............................................. G01N 27/58
[52] U.S. Cl. ..................................... 204/422; 204/423
[58] Field of Search ............... 204/422, 423, 424, 421, 204/425, 426, 427, 428, 429, 1 S

[56] References Cited

U.S. PATENT DOCUMENTS

| | | | |
|---|---|---|---|
| 3,841,987 | 10/1974 | Friese et al. | 204/427 |
| 4,045,300 | 8/1977 | Renet | 204/1 T |
| 4,342,633 | 8/1982 | Cure | 204/423 |
| 4,399,022 | 8/1983 | Nakajima et al. | 204/422 |
| 4,451,350 | 5/1984 | Tsuchida et al. | 204/422 |

Primary Examiner—G. L. Kaplan
Attorney, Agent, or Firm—Robert R. Hubbard; Joseph P. Abate

[57] ABSTRACT

An expandable immersion oxygen sensor for molten metal is provided with an improved oxygen reference electrode including Cr, $Cr_2O_3$, NiO, and Fe and the oxygen electrode and thermocouple are secured in the face of the sensor by resin-sand to reduce initial overshoot and failure due to thermal shock.

5 Claims, 1 Drawing Figure

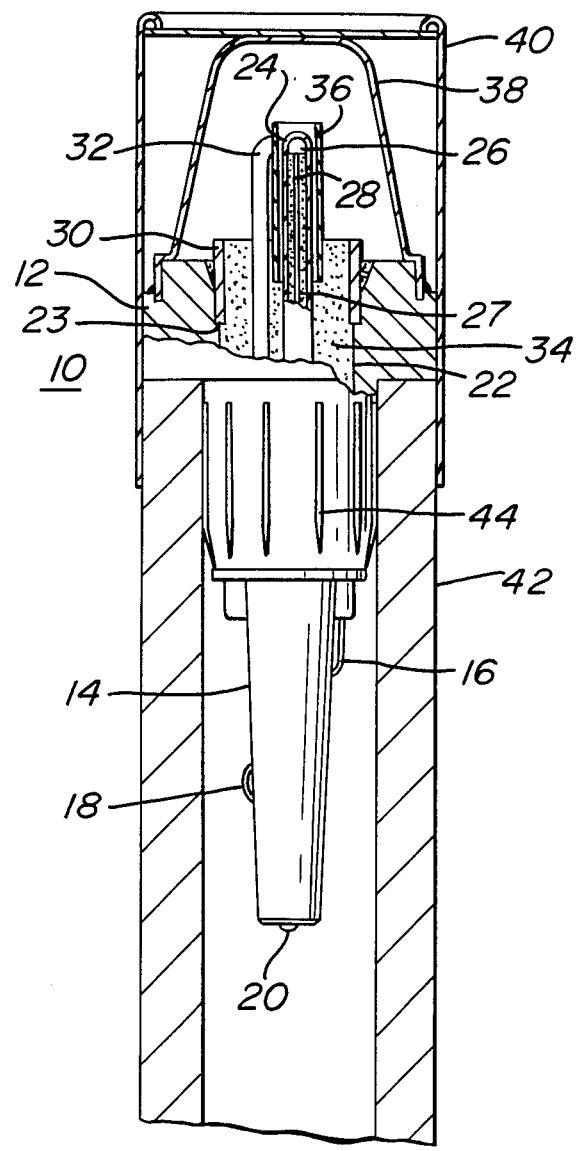

OXYGEN SENSOR

This is a continuation of application Ser. No. 862,735 filed May 13, 1986, now abandoned.

This invention relates to expendable immersion oxygen sensors capable of being immersed in a bath of molten metal for the determination of the oxygen dissolved in the metal and, more particularly, to an oxygen sensor for use with molten iron or steel.

BACKGROUND OF THE INVENTION

The determination of dissolved oxygen in iron and steel by immersing an electrolytic cell and temperature sensing device into the molten metal during the refining of steel has been practiced by steel companies for sometime. Because of the manner in which these oxygen sensors are used the solution of any problem resulting in failure of the sensor to provide a proper output signal must be based upon assumptions as to the cause of such failure.

While there has been much improvement in the reliability of the reading from the oxygen sensor over the years, there continues to remain the problem of initial overshoot of the output signal from the oxygen sensor upon immersion of the sensor into the bath of molten metal, particularly when the sensor is used with iron or steel having low levels of oxygen, in the 2 to 3 parts per million range. Furthermore, while the problem of thermal shock associated with the magnesium stabilized zirconium oxide electrolyte has received much attention and several solutions have been proposed, there still remains failure of some of the sensors to produce the proper output signal due to breakage of the solid electrolyte as a result of thermal shock.

SUMMARY OF THE INVENTION

The present invention is directed to an expendable oxygen sensor for measuring the dissolved oxygen in a bath of molten metal and, more particularly, in a bath of molten steel. The device comprises a measuring cartridge which is generally sealingly mounted in the end of a rigid tube of heat insulating material capable of withstanding the temperature of the molten steel for an immersion time of 15 seconds.

The cartridge has a cylindrical body portion with the oxygen determining electrolytic cell protruding from one face of the cylinder, electrical leads passing through the cylinder and electrical contact members formed in the opposite end of the body portion. The electrolytic cell, which contains a reference electrode within a tube of solid electrolyte, is mounted within a cavity in the end face of the body portion with the cell protruding beyond the face of the body and usually secured there by a refractory cement.

According to the present invention improved sensor response is achieved with the electrolytic cell secured to the body portion by resin-sand and by change in the material of the reference electrode.

It is an object of the present invention to provide a novel immersion oygen sensor which eliminates the problem of initial overshoot upon immersion into a molten metal bath.

It is another object of this invention to reduce the failures of immersion oxygen sensors due to thermal shock occuring at the time of immersion.

BRIEF DESCRIPTION OF THE DRAWING

For an understanding of applicant's invention the following description and claims should be read with reference to the accompanying drawing wherein:

The sole FIGURE is a side elevation of an immersion oxygen sensor partially in cross section.

DETAILED DESCRIPTION OF THE DRAWING

Referring now to the drawing, there is shown an immersion oxygen sensor cartridge 10 which, as shown, consists of a body portion 12 and a tailpiece member 14. The body portion 12 and the tailpiece member 14 may be a monolithic structure or may, as shown, be two separate pieces that are secured together either by cement or by mechanical latching or by both. Secured to and carried by the tailpiece member 14 are a series of three electrical contacts 16, 18 and 20 to provide electrical signal connections to the cartridge 10. Preferably the tailpiece member 14 should be constructed of a resilient material such, for example, as nylon or polystyrene. The resiliency of the material insures that the contacts 16, 18 and 20 will make good electrical connection with corresponding contacts in a manipulator (not shown) and also provide adequate friction force so that the cartridge and the manipulator will not separate prematurely during use.

The face of the body portion 12 contains a cavity or opening 22 for housing and securing the proximal ends of the various elements constituting the dissolved oxygen sensor. The open end of a closed end tube 24 of magnesium stabilized zirconium oxide is inserted into the cavity 22 with the closed end of the tube 24 protruding beyond the face of the body portion 12. The tube 24 of magnesium stabilized zirconium oxide is the solid electrolyte of an oxygen electrochemical cell. Contained within the closed end of the tube 24 is an oxygen reference material 26 that preferably is in powdered form. Located between the oxygen reference material 26 and the open end of the tube 24 is a quantity of $Al_2O_3$ powder 27, as an inert filler to maintain the reference material 26 in contact with the inner closed surface of the tube 24. The powder 27 is retained within the tube 24 by an epoxy cement in the opening of the tube 24.

In order to provide an electrical connection to the reference side of the solid electrolyte 24, an electrical conductor 28, preferably a molybdenum wire, extends through the open end of the tube 24 and into the reference material 26. The electrical contact 16 is connected generally by a suitable conductor (not shown) to the end of the electrical conductor 28.

Upon immersion of the oxygen sensor cartridge 10 into a bath of molten metal, an oxygen electrochemical cell is completed. The molten metal bath forms an unknown oxygen level on the bath side of the solid electrolyte, and a known reference oxygen level is produced on the inner side of the solid electrolyte. In order to provide an electrical connection to the bath side of the solid electrolyte an electrical conductor 30 in the form of a steel ring is located in the face of the cavity 22. The conductor 30, which may alternatively be in the form of a protruding molybdenum rod, is connected by a conductor (not shown) to the electrical contact 20. As shown, the wall of the cavity or opening 22 is provided with a shoulder 23 to insure that the ring conductor 30 protrudes beyond the face of the body portion 12. Thus, upon immersion of the cartridge 10 into a bath of molten metal, an electrical signal is produced between the contacts 16 and 20 that is determined by the difference in the oxygen levels in the bath of molten metal and the reference electrode and by the temperature of the bath.

In order to determine the oxygen in the bath it is necessary to measure the temperature of the bath. It is, therefore, normal practice to include in an immersion oxygen sensor cartridge a bath temperature measuring element, usually in the form of a thermocouple. Thus, the cartridge in the figure is shown as including a U-shaped tube 32 made of quartz, or the like, in which is located a thermocouple junction preferably of Pt;Pt, 10% Rhodium. The thermocouple leads are electrically connected to the contacts 16 and 18, with the Pt lead of the thermocouple connected to the contact 16 and the Pt, 10% Rhodium lead connected to the contact 18.

Applicant has noted that upon immersion of a conventional oxygen sensor into a bath of molten metal that the recorded values of the oxygen, as produced on a chart recording instrument, often climb rapidly to a high level of indicated oxygen and then decrease to a steady value representative of the oxygen level of the bath. Applicant discovered that the undesirable initial overshoot of the oxygen level could be, for the most part, eliminated by changing the composition of the oxygen reference material 26 by using a powder mixture having 86%, Cr; 3%, $Cr_2O_3$; 7%, Nio; and 4%, Fe. While the addition of the NiO and Fe to the reference material 26 improved the response of the oxygen sensor by reducing the occurrence of an initial overshoot it was noted by applicant that initial overshoot continued to exist when the oxygen sensor was used to measure oxygen in metals having low oxygen concentrations, in the order of 2 to 3 parts per million.

It has been conventional practice to secure the tube 24, the U-shaped tube 32, and the electrical conductor 30 in the cavity 22 by using a water slurry of refractory cement and then heating the cartridge 10 to dry the water from the cured cement. Applicant has discovered that if a resin sand is used to secure the measuring elements in the cavity 22 in place of the refactory cement, the initial overshoot when using the oxygen sensor even in measuring oxygen in low concentrations is minimized. Accordingly, the oxygen sensor cartridge 10 shown in the figure has the cavity 22 filled with a resin-sand 34. Applicant believes that the initial overshoot occurring in the measurement of oxygen in metals having low oxygen concentrations when using conventional sensors with refactory cement results from the liberation of some residual water vapor from the refractory cement. Since resin-sand does not use water in its composition there is no chance of liberation of water vapor from the cartridge upon immersion. Resin-sand is well known to those skilled in the art as a mixture of silica sand with a binder of phenol formaldehyde.

In the manufacture of the oxygen sensor cartridge 12 the resin-sand is placed in the cavity 22 and in any annular spaces occurring outside the ring conductor 30. The cartridge is then baked to cause the resin binder to set and thereby secure the sensor elements in cavity 22.

Because of the low thermal conductivity and high thermal mass of the resin-sand, as compared to the refractory cement, it has been found that another benefit of the use of the resin-sand 34 is that the longitudinal temperature gradient in the magnesium stabilized zirconium oxide tube 24 is reduced, and the tube has less tendency to fracture due to thermal shock when the cartridge 10 is immersed in molten metal.

In order further to reduce the thermal shock breakage of the tube 24, an open ended steel tube 36 surrounds the tube 24 and extends beyond the closed end of the tube 24. The steel tube 36 is of such an inner diameter that it does not contact the tube 24, but provides an air space between the tube 24 and the tube 36. In practice, the tube 36 is made of a corrosion resistant steel to eliminate any possibility of rusting of the steel tube 36, which might adversely affect measurements of oxygen at low concentrations.

In order to use the cartridge in the measurement of oxygen in an industrial environment where slag is normally present on the surface of the molten metal, the face of the cartridge and the sensing elements are protected from the slag during immersion by a steel cap 38, secured by epoxy to the face of the body portion 12, and an outer cap 40, preferably made of paper. The caps 38 and 40 protect the face of the cartridge 10 during immersion through the slag layer and then quickly melt or burn away when the cartridge is in the molten metal to expose the oxygen cell and the thermocouple to the molten metal.

In order to immerse the cartridge in the bath of molten metal the cartridge 10 is secured in the end of a long tube 42 capable of immersion in the molten metal and having heat insulating properties. Typically the tube 42 is made of cardboard. For measurement at low levels of oxygen in molten metal, all silica containing components and combustible components, such as paper tube 42, are coated or replaced with more stable oxide components or coatings, typically $Al_2O_3$ or MgO. The body portion 12 has a cylindrical extension of reduced diameter with ridges 44 on its outer cylindrical surface. Epoxy cement is applied to the part of the body portion 12 that contacts the tube 42 and the two are positioned together, as shown in the figure.

It is conventional practice to slide the assembled tube 42 and cartridge 10 onto a manipulator usually in the form of an elongated pipe with lead wires passing through the pipe and terminating in a connector element that has contact members that engage the contacts 16, 18 and 20. The electrical signals generated by the oxygen cell and the thermocouple are thereby transmitted through the manipulator to measuring and recording instruments to display the temperature and oxygen level in said molten metal.

The present invention may be embodied in other specific forms and reference should be made to the appended claims as indicating the scope of the invention.

What is claimed is:

1. An improved immersion oxygen sensor having an electrical output that is more stable and less susceptible to initial overshoot of the measured value upon immersion in a bath of molten metal comprising a zirconia solid electrolyte having its outer surface exposed to said molten metal upon immersion in said bath, a Cr, $Cr_2O_3$ reference electrode contacting the inner surface of said solid electrolyte to provide a reference level of oxygen partial pressure, a first electrical conductor providing electrical contact with said reference electrode, and a second electrical conductor for making electrical contact with said molten metal upon immersion, characterized in that NiO and Fe are combined in said reference electrode.

2. An improved oxygen sensor capable of immersion in a bath of molten metal for the determination of dissolved oxygen content in said bath comprising a sensor cartridge having a body portion with a cavity in one face of said body portion, a closed end tube of solid electrolyte mounted in said cavity with said closed end of said tube extending beyond said surface of said cartridge, an oxygen reference material mounted within said closed end tube and in contact with the inner surface of said tube, a first electrical conductor extending through said cartridge and into said closed end tube making electrical contact with said oxygen reference material, a second electrical conductor extending through said cartridge to provide electrical contact with said bath of molten metal when said sensor is immersed in said bath, and a resin-sand material filling said cavity to maintain said closed end tube securely in said cartridge.

3. Apparatus as claimed in claim 2 in which said oxygen reference material is a mixture of $Cr$, $Cr_2O_3$, $NiO$ and $Fe$.

4. Apparatus as claimed in claim 2 in which a heat shield in the form of an open ended metal cylinder supported by said resin-sand material surrounds said closed end tube of solid electrolyte with a space between said cylinder and said tube and said cylinder extends beyond said closed end of said tube.

5. Apparatus as claimed in claim 4 in which said metal cylinder is formed of steel.

* * * * *